US009827269B2

(12) United States Patent
Sahin et al.

(10) Patent No.: US 9,827,269 B2
(45) Date of Patent: Nov. 28, 2017

(54) APPLICATION OF STEM CELLS IN THE ORTHODONTIC MAXILLARY EXPANSION

(71) Applicant: YEDITEPE UNIVERSITESI, Istanbul (TR)

(72) Inventors: Fikrettin Sahin, Istanbul (TR); Mehmet Emir Yalvac, Istanbul (TR); Abdullah Ekizer, Kayseri (TR); Tancan Uysal, Izmir (TR); Mehmet Fatih Sonmez, Kayseri (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 145 days.

(21) Appl. No.: 14/433,677

(22) PCT Filed: Oct. 4, 2013

(86) PCT No.: PCT/IB2013/002203
§ 371 (c)(1),
(2) Date: Apr. 6, 2015

(87) PCT Pub. No.: WO2014/053906
PCT Pub. Date: Apr. 10, 2014

(65) Prior Publication Data
US 2015/0231179 A1    Aug. 20, 2015

(30) Foreign Application Priority Data
Oct. 5, 2012    (TR) .................................. 201111423

(51) Int. Cl.
*A61K 35/28*    (2015.01)
*A61C 7/10*    (2006.01)

(52) U.S. Cl.
CPC ................ *A61K 35/28* (2013.01); *A61C 7/10* (2013.01)

(58) Field of Classification Search
CPC .................................. A61K 35/28; A61C 7/10
See application file for complete search history.

(56) References Cited

U.S. PATENT DOCUMENTS

| 2009/0148419 A1 | 6/2009 | Gonzalez De La Pena et al. |
| 2010/0172863 A1* | 7/2010 | Wasielewski ........ A61K 9/0009 424/85.2 |

(Continued)

FOREIGN PATENT DOCUMENTS

| WO | WO2008008114 | 1/2008 |
| WO | WO2009046346 | 4/2009 |

OTHER PUBLICATIONS

Hwang, Yun-Jang and Choi, Jin-Young;Addition of Mesenchymal Stem Cells to the Scaffold of Platelet-Rich Plasma Is Beneficial for the Reduction of the Consolidation Period in Mandibular Distraction Osteogenesis, 2010; American Association of Oral and Maxillofacial Surgeons.*

(Continued)

*Primary Examiner* — Christopher Beccia
(74) *Attorney, Agent, or Firm* — Gokalp Bayramoglu

(57) ABSTRACT

This invention relates to the contributions of the bone marrow—and adipose tissue—derived mesenchymal stem cells applied following the maxillary expansion—a frequently used method for the orthodontic treatment—to the healing of the expanded bone tissues. In the invention, adipose tissue and bone marrow-derived stem cell applications increased the healing and quality of the bones following the maxillary expansion and the applied stem cells were involved in the bone structure. Thus, the relapse following the maxillary expansion treatment was avoided. This application will shorten the treatment period for patients undergoing the maxillary expansion treatment and the patients will not have to use apparatus for a long period of time.

7 Claims, 3 Drawing Sheets

(56) References Cited

U.S. PATENT DOCUMENTS

| | | | | |
|---|---|---|---|---|
| 2011/0269095 A1* | 11/2011 | Singh | | A61F 5/566 433/24 |
| 2012/0014921 A1* | 1/2012 | Kramer | | A61K 35/30 424/93.2 |

OTHER PUBLICATIONS

Database Medline [Online] US National Library of Medicine (NLM), Bethesda, MD, US; Nov. 2009 (Nov. 2009), Kim Su-Hwan et al:"Alveolar bone marrow stem cells in a canine peri-implant defect model: a plot study.", xp002721860.

Behn1A H et al: "Secondary repair of alveolar clefts using human mesenchymal stem cells", Oral Surgery, Oral Medicine, Oralpathology, Oral Radiology and Endodontics, Mosby-Year Book, St. Louis, MO, US, vo 1. 108, No. 2, Aug. 1, 2009 (Aug. 1, 2009), pp. e1-e6, XP026319141, ISSN:1079-2104.

Liang Zhang et al:"In vivo alveolar bone regeneration by bone marrow stem cellsjfibrin glue composition", Archives of Oral Bi0logy, vo I. 57, No. 3, Mar. 1, 2012 (Mar. 1, 2012), pp. 238-244, XP055107888, ISSN: 0003-9969.

Database Medline [Online] US National Library of Medicine (NLM), Bethesda, MD, US; Sep. 2011 (Sep. 2011), Ito Kenji et al: "Osteogenic potential of effective bone engineering using dental pulp stem cells, bone marrow stem cells, and periosteal cells for osseointegration of dental implants.", XP002721861.

El1sabet Farre-Guasch et al: "Buccal Fat Pad , an Oral Access Source of Human Adipose Stem Cells with Potential for Osteochondral Tissue Engineering: An In Vitro Study", Tissue Engineering Part C: Methods, vol. 16, No. 5, Oct. 1, 2010 (Oct. 1, 2010), pp. 1083-1094 , XP055107367, ISSN: 1937-3384.

H1cok Kev1n C et al: "Human adipose-derived adult stem cells produce osteoid in vivo", Tissue Engineer1ng, Larchmont, NY, US, vol. 10, No. 3-4, Mar. 1, 2004 (Mar. 1, 2004) pp. 371-380, XP002495882, ISSN: 1076-3279.

Mes1mak1 K et al: "Novel maxillary reconstruction with ectopic bone formation by GMP adipose stem cells", International Journal of Oral and Max1llofac1al Surgery, Copenhagen, DK, vo 1.38, No. 3, Mar. 1, 2009(Mar. 1, 2009), pp. 201-209, XP025985286, ISSN: 0901-5027.

Shanna M. W1lson et al: Adipose-Derived Mesenchymal Stem Cells Enhance Healing of Mandibular Defects in the Ramus of Swine, Journal of Oral and Max1llofac1al of Oral and Max1llofac1al Surgery, vol. 70, No. 3, Mar. 1, 2012 (Mar. 1, 2012), pp. e193-e203, XP055108049, ISSN: 0278-2391.

Hwang Y J et al: "Addition of Mesenchymal Stem Cells to the Scaffold of Platelet-Rich Plasma Is Beneficial for the Reduction of the Consolidation Period in Mandibular Distraction Osteogenesis" Journal of Oral and Max1llofac1al Surgery, Saunders, Philadelphia, PA, US, vo 1.68, No. 5, May 1, 2010 (May 1, 2010), pp. 1112-1124, XP027012254.

J. D. A. Gurgel et al: "Ossification of the midpalatal suture after surgically assisted rapid maxillary expansion", The European Journal of Orthodontics, vol. 34, No. 1, Feb. 1, 2012 (Feb. 1, 2012), pp. 39-43, XP055108245, ISSN:0141-5387.

Zongyang Sun et al: of Autologous Mesenchymal Stem Cells for Mandibular Distraction Osteogenesis: Preliminary Studies in a Porcine Mode, PLOS ONE, vol. 8, No. 9, Sep. 15, 2013 (Sep. 15, 2013), p. e74672, XP055108064, ISSN: 1932-6203.

Sanoor George K et al: Adipose Stem Cell Tissue-Engineered Construct Used to Treat Large Anterior Mandibular Defect: A Case Report and Review of the Clinical Application of Good Manufacturing Practice-Level Adipose Stem Cells for Bone Regeneration 11 Journal of Oral and Maxillofacial Surgery, vol. 71, No. 5, Feb. 1, 2013, p. 938-950.

Wertz R, Dreskin M. Midpalatal suture opening: a normative study. Am J Orthod 1977; 71: 367-381.

McNamara JA. Maxillary transverse deficiency. Am J Orthod Dentofacial Orthop 2000; 117:567-570.

Bishara SE, Staley RN. Maxillary expansion: Clinical implications. Am J Orthod Dentofacial Orthop 1987; 91:3-14.

Saito S. Shimizu N. Stimulatory effects of low-power laser irradiation on bone regeneration in midpatatal suture during expansion in the rat. Am J Orthod Dentofacial Orthop 1997; 111: 525-532.

Sawada M, Shimizu N. Stimulation of bone formation in the expanding mid-palatal suture by transforming growth factor-beta 1 in the rat. Eur J Orthod 1996; 18: 169-179.

Chang HN, Garetto LP, Potter RH, Katona TR, Lee CH, Roberts WE. Angiogenesis and osteogenesis in an orthopedically expanded suture. Am J Orthod Dentofacial Orthop 1997; 111: 382-390.

Uysal T, Ustdal A, Sonmez MF, Ozturk F. Stimulation of bone formation by dietary boron in an orthopedically expanded suture in rabbits. Angle Orthod 2009;79:984-990.

Uysal T, Amasyali M, Olmez H, Karslioglu Y, Gunman O. Stimulation of bone formation in the expanding inter-premaxillary suture by vitamin E, in rat. Korean J Orthod 2009; 39:337-347.

Uysal T, Amasyali M, Enhos S, Sonmez MF, Sagdic D. Effects of ED-71, a new active vitamin D analog, on bone formation in an orthopedically expanded suture in rats. a histomorphometric study. Eur J Dent 2009;3: 165-172.

Uysal T, Amasyali M, Olmez H. Enhos S, Karslioglu Y, Gunman O. Effect of vitamin C on bone formation in the expanded inter-premaxillary suture. Early bone changes. J Orofac Orthop 2011; 72:290-300.

Uysal T, Amasyali M, Olmez H, Karslioglu Y, Gunhan O. Stimulation of bone formation by direct electrical current in an orthopedically expanded suture in rat. Korean J Orthod 2010;40(2)106-114.

De Ugarte DA, Morizono K, Elbarbary A, Alfonso Z, Zuk PA, Zhu M, Dragoo JL, Ashjian P, Thomas B, Benhaim P, Chen I, Fraser J, Hedrick MH (2003) Comparison of multi-lineage cells from human adipose tissue and bone marrow. Cells Tissues Organs 174: 101-109.

Deslex S, Negrel R, Vannier C, Etienne J, Ailhaud G (1987) Differentiation of human adipocyte precursors in a chemically defined serum-free medium. Int J Obes 11: 19-27.

Aust L, Devlin B, Foster SJ, Halvorson YD, Hicok K, Du Laney T, Sen A, Willingmyre GD, Gimble JM (2004) Yield of human adipose-derived adult stem cells from liposuction aspirates. Cytotherapy 6: 7-14.

Duijvestein M, Vos AC, Roelofs H, Widenberg ME, Wendrich BB, Verspaget HW, Kooy-Winkelaar EM, Koning F, Zwaginga JJ, Fidder HH, Verhaar AP, Fibbe We, Van Den Brink GR, Hommes DW. Autologous bone marrow-derived mesenchymal stromal cell treatment for refractory luminal Crohn's disease: results of a phase I study. Gut. Dec. 2010;59(12):1662-1669.

Gao J, Dennis JE, Muzic RF, Lundberg M. Caplan AI.Cells TissuesOrgans 2001:169:12-20. TheDynamic in vivoDistribution of Bone Marrow-Derived MesenchymalStemCells afterinfusion.

Tholpady SS, Katz AJ, Ogle RC. Mesenchymal stem cells from rat visceral fat exhibit multipotential differentiation in vitro. Anat Rec Part A 2003;272A:398-402.

* cited by examiner

APPLICATION OF STEM CELLS IN THE ORTHODONTIC MAXILLARY EXPANSION

TECHNICAL FIELD

This invention relates to the method in which stem cells derived from bone marrow and adipose tissue are used in orthodontic maxillary expansion.

PREVIOUS TECHNIQUE

Maxillary narrowness is a unilateral or bilateral skeletal problem in the jaw bones. This problem may occur as a result of the reduction in the mandibular and maxillary width in terms of bone level. For the treatment of orthodontic patients with maxillary narrowness, the expansion apparatus supported by the teeth are used. The use of these apparatus enables the expansion of the maxilla. After the expansion treatment, new bone formation is expected to occur. The relapse of the achieved expansion is prevented through bone formation.

In the study by Wertz and Dreskin, it was stated that in individuals between the ages of 8 and 29 years, there was a mean increase of 6.5 mm between the molar teeth with the use of rapid maxillary expansion, and that during the stabilization and retention period. 30% of this increase was relapsed and besides, in the oldest patients, the relapse rate in the intermolar distance was reported to rise to 75% (1). In the technique, the relapse rates reported after the maxillary expansion were known to be very high.

Following the maxillary expansion, new bone formation is required for the maintenance of the achieved state and for the stabilization of the occlusion. Therefore, a reinforcement treatment is administered via movable or fixed appliances for 3 to 6 months (2, 3).

The shortening of the reinforcement period after the maxillary expansion is essential for the treatment success and patient cooperation. However, the shortening of this period is unlikely to be achieved due to the relapse occurring after the expansion. Moreover, the tendency to relapse after maxillary expansion may last for many years.

In order to obtain more effective results in a shorter period, it is important to evaluate the factors affecting bone healing and reorganization. For this reason, the quality and rate of new bone formation to occur between the surfaces of osteotomized bone segments are important factors to reduce early relapse. The shortening of this period will also shorten the time of long orthodontic treatment period and increase the patient cooperation.

Recently, in the technique, there are studies to increase bone formation in the suture and its quality, and thus protecting the stability (4-6). In fact, the importance of the bone formation in the suture is known long before. The maintenance of the increase achieved in the arch width by opening midpalatal suture is known to be enabled following a repair of the bone defect in the suture with a new bone.

Considering the fact that relapse can be reduced by speeding up the bone formation in the midpalatal suture, Saito and Shimizu (4) applied low-level laser therapy to the expanded sutura and determined that bone regeneration was increased. Uysal et al. showed that boron mineral in rabbits (7), vitamin E (8), vitamin D (9), vitamin C (10) and electrical stimulation (11) in rats increased the bone formation during the maxillary expansion. During these experimental studies, the osteogenic activities of the administered agents, and the cellular activities of stem cells in the bone formation in this region were not evaluated.

In many studies to date, it has been demonstrated that mesenchymal stem cells derived from bone marrow and adipose tissue (BMMSCs, ATMSCs) considerably increased the bone regeneration, Since MSCs are of mesodermal origin, they have the potential to transform into bone tissues (12). Both bone marrow and adipose tissue are clinically easily isolatable tissues (13, 14). The re-transplantation of these isolated tissues to the same patient is called autologous transplantation. Bone marrow and adipose tissue transplantations are successfully applied in the clinical setting during the studies so far (15). The clinical use of these autologous stein cell resources are known not to cause any ethical problem.

United States Patent Application No. 20090148419, which is one of the known applications in the technique, refers to the use of a particular type of adipose tissue derived from mesenchymal stem cells in the treatment of the graft-versus-host disease.

International Patent document No. WO2008008114, which is also a known application in the technique, refers to the use of stem cells derived from adipose tissue in the treatment of Krabbe disease.

International Patent document No. WO2009046346, which is also a known application in the technique, refers to the stem cell therapy to be used for the treatment of obesity.

SUMMARY OF THE INVENTION

The purpose of this invention is to enable new bone formation in the midpalatal suture after maxillary expansion by using stem cells from both adipose tissue and bone marrow.

The other purpose of the invention is to administer a stem cell therapy which prevents patients from having to use apparatus for a long period of time during the maxillary expansion treatment.

Another purpose of the invention is to administer a stem cell therapy which shortens the treatment period for the patients undergoing maxillary expansion.

Yet another purpose of the invention is to administer a stem cell therapy which enables an increase in the area and quality of the newly formed bone structures.

BRIEF DESCRIPTION OF THE DRAWINGS

The figures showing the results obtained from the experimental studies conducted in order to reach the goal of this invention are enclosed and are as follows.

DETAILED DESCRIPTION OF THE INVENTION

Experimental Study

Figure 1:
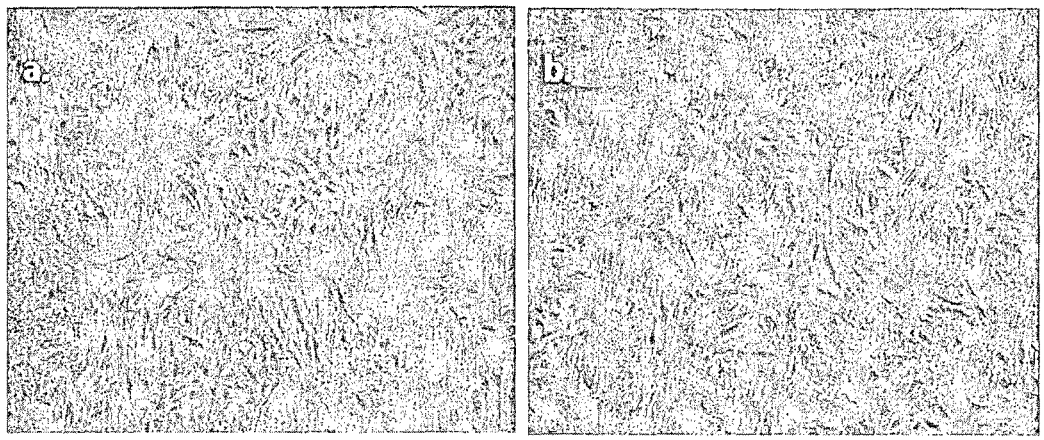
FIG. 1—In vitro morphological appearances of ATMSCs (a) and BMMSCs (b).

The experimental study and its results providing a basis for the developed model are indicated below.

The Isolation and Characterization of Stem Cells

The isolation of BMMSCs and ATMSCs from 3-month-old Wistar rats was conducted with known applications in the technique (16, 17). In order to characterize the obtained stein cells, they were analyzed through flow cytometry and then, their in vitro bone-forming potentials were shown.

Maxillary Expansion in Rats 30 male Wistar rats were distributed in three equal groups. In each group, one single helix of 2 mm in diameter bent from stainless steel wire of 0.014 inches and a spring with arms of 10 mm each were used to expand mid-palatal suture. The activation was made on a millimetric paper and was adjusted to apply a strength of 30 grams.

Under general anesthesia, upper two incisors were drilled with holes on front and hack sides at the level of gingival edges (papilla) and the expansion apparatus was placed into these holes from the front of the teeth.

Injection of the Stem Cells

Twenty-four hours following the placement of the expansion apparatus, ATMSCs in the group 1, BMMSCs in the group 2 and normal saline in the group 3 (control group) were injected into the mid-palatal suture region. Stem Cells were prepared in 100 μl of PBS (Phosphate-Buffered Saline) and then injected using insulin needles into the mid-palatal suture region (1 million cells per rat). Following an expansion period of five days, the expansion apparatus was removed and brackets were placed in the holes drilled on the incisors for reinforcement. Following a reinforcement period of 10-14 days, the animals were sacrificed by applying high doses of anesthetics.

Histomorphometric Assessment

For the evaluation of hard tissue, the upper jaws of ten animals each from the control and experimental groups were dissected (elimination of the soft tissues) and fixated in a solution of 10% formalin. After the fixation, the brackets used for the reinforcement purposes were removed and the premaxilla was decalcified in 5% formic acid. The sections were obtained at vertical angles to the sagittal plane. The reference points were determined as the apex and 4 mm apical to the alveolar crest. The line passing through the reference planes is along the centre of the incisor crown at the level of gingiva. The samples were embedded in paraffin blocks and serial sections of 5 μm thickness were obtained. The histological sections were stained with hematoxylin-eosin and then the histomorphometric assessment was conducted.

In Vivo Tracking of the Transplanted Stem Cells

In order to determine the vitality of transplanted stem cells in the mid-palatal suture region, the bone marrow- and adipose tissue-derived stem cells were marked with PKH167 green (Sigma) cell membrane dye and then injected into the rats. After the conclusion of the experiment, the premaxilla dissected from the rats was frozen on dry ice and then serial sections were obtained with cryotome. The obtained sections were fixated and examined under fluorescence microscopy, and then the presence of the marked stem cells was identified.

Results of the Experiment

The stem cells obtained from 3-month-old Wistar rats were demonstrated to be similar to MSCs (Mesenchymal Stem Cells) through flow cytometry (Table 1) and differentiation experiments.

TABLE 1

The characterization of ATMSCs and BMMSCs through flow cytometry

| Cell Type | CD29 | CD90 | CD106 | CD14 | CD34 | CD45 |
| --- | --- | --- | --- | --- | --- | --- |
| ATMSCs | + | + | + | - | - | - |
| BMMSCs | + | + | + | - | - | - |
| | MSC markers | | | Hematopoietic markers | | |

The results of the flow cytometry showed that ATMSCs and BMMSCs are positive for MSC markers and negative for hematopoietic markers.

When ATMSCs and BMMSCs were examined under in vitro microscope, it was observed that they had classic MSC morphology (FIG. 1).

Figure 2:
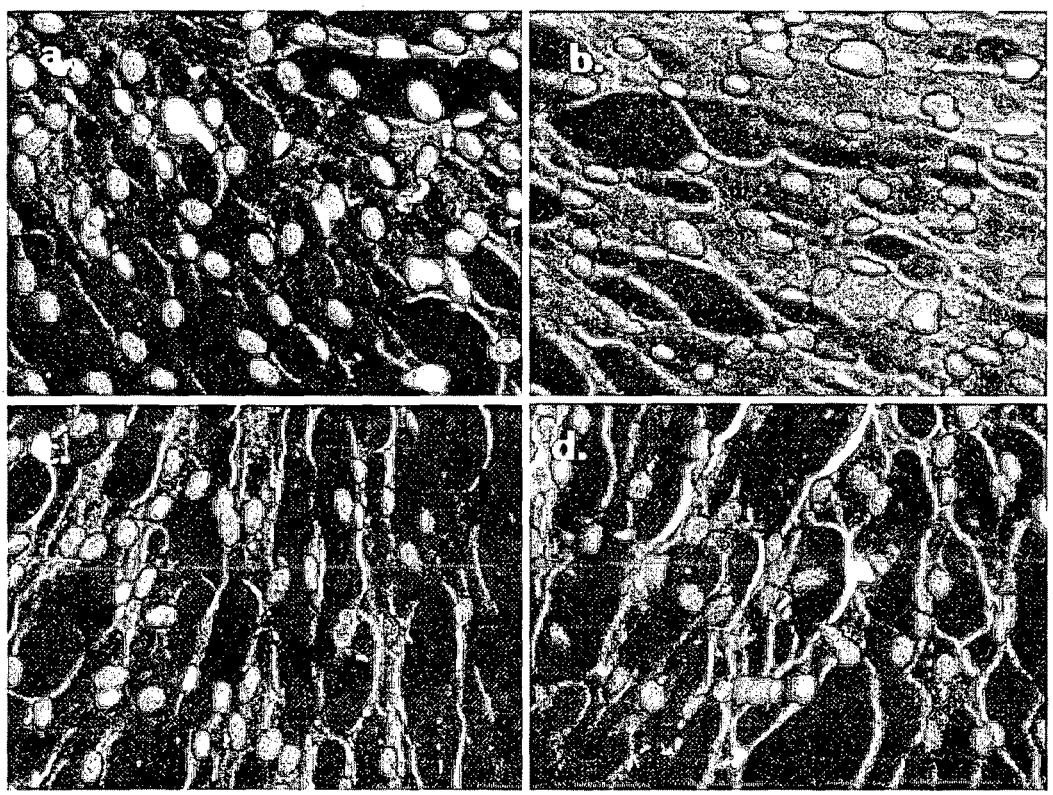
FIG. 2—Osteocalcin staining: a. ATMSCs, b. BMMSCs; Collagen type 1 staining, c. ATMSCs and d. BMMSCs—The appearances of the differentiation experiment results of ATMSCs and BMMSCs.

The potentials of ATMSCs and BMMSCs to differentiate into bone cells were shown and it was also shown that these cells produced bone markers—collagen type 1 and osteocalcin proteins—as a result of the differentiation (FIG. 2).

Figure 3:
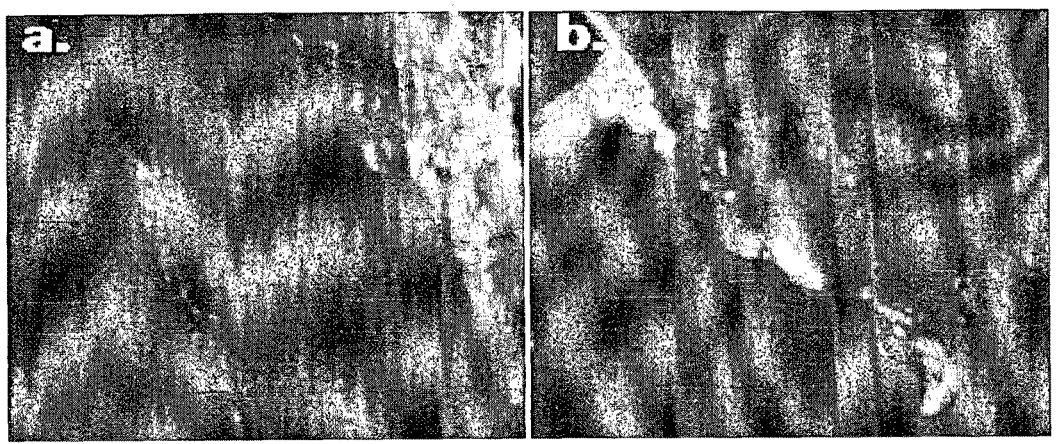
FIG. 3—a. ATMSCs and b. BMMSCs—The appearances of premaxillary tissue under fluorescence microscopy.

10-14 days following the application of ATMSCs and BMMSCs into the rats that had undergone maxillary expansion, the dissected premaxillary tissue was examined under the microscope and the presence of the marked stem cells was identified in the premaxillary tissue (white areas are injected cells a. ATMSCs and b. BMMSCs) (FIG. 3).

Figure 4:
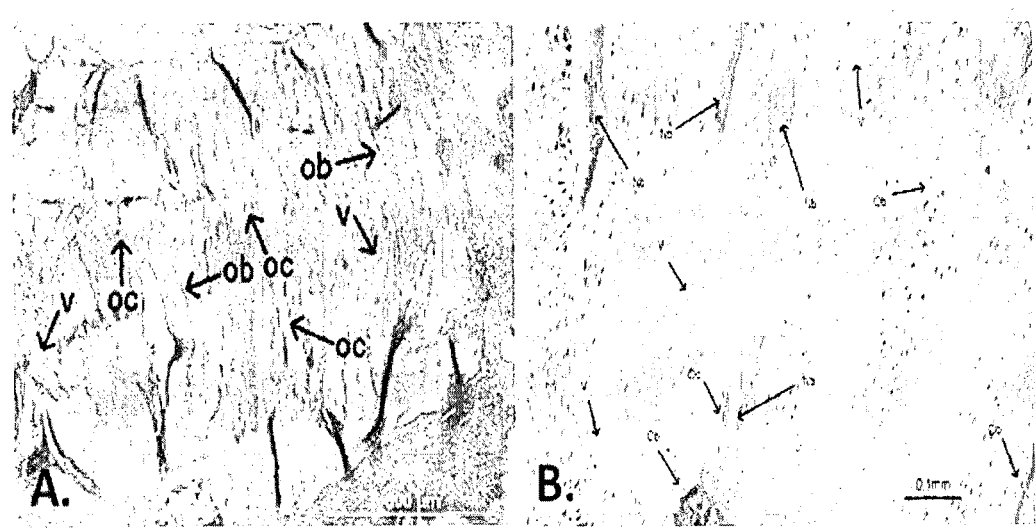
FIG. 4—A. Osteoblasts (ob), osteoclasts (oc) and vessels (v) formed through the application of BMMSCs in the mid-sutural region. B. Osteoblasts (ob), osteoclasts (oc) and vessels (v) formed through the application of ATMSCs in the mid-sutural region; the appearances of the new bone formations in the mid-palatal suture region.
Figure 5:
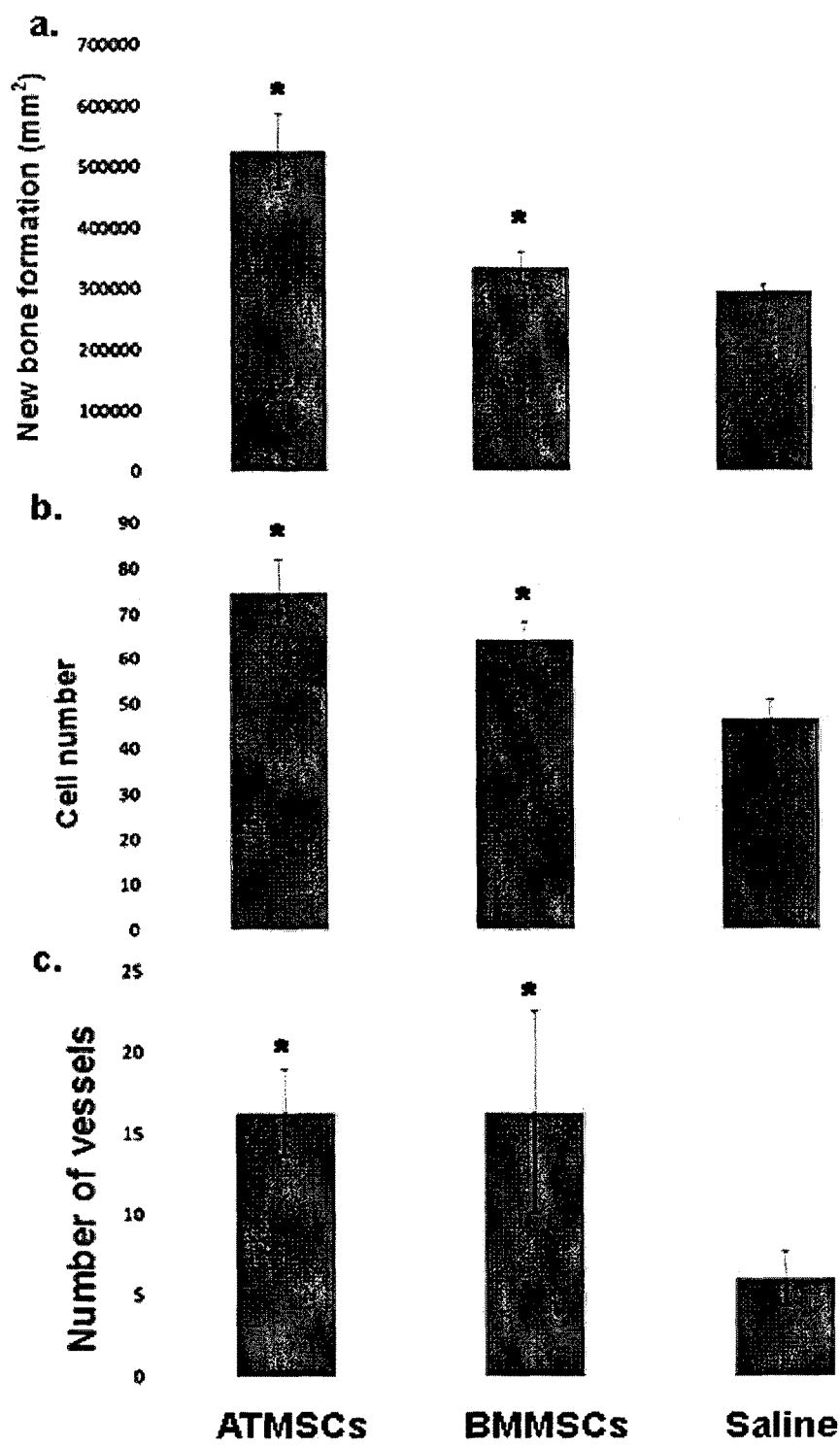
FIG. 5—The appearance of the histomorphometric analysis of the new bone formation in the mid-palatal suture region; a. The comparison of the bone formation in the suture region; b. The comparison of the number of osteoblasts in the suture region; c. The comparison of the number of vessels in the suture region.

The newly formed osteoblasts (ob), osteoclasts (oc) and vessels (v) in the mid-palatal suture region in the groups that had undergone stem cell application were identified through the histological assessment (FIG. 4). The histomorphometric assessment of the new bone formation in the mid-palatal suture region showed that the stem cell application provided a more effective bone formation compared to the negative control group (in which only normal saline was applied). The application of ATMSCs and BMMSCs enabled faster bone formation in the mid-palatal suture region following the maxillary expansion, and it also increased the number of osteoblasts and vessels in the mid-palatal suture region (FIG. 5).

The fact that it was experimentally proved that the application of ATMSCs and BMMSCs accelerated the new bone formation in the mid-palatal suture region and that those stem cells were directly involved in the bone structures through the process of new bone formation paved the way for the new treatment methods. This invention with the obtained findings can be applied to all mammals including humans.

The shortening of the orthodontic treatment period with stem cell therapies, reduction of the relapse rate and thus achieving more stable results and improving the comfort of both patients and physicians are the advantages of this invention. The orthodontic treatment period, which gives a hard time for the patients since having to wear an apparatus during the treatment is esthetically unpleasant and also causes discomfort in their mouths, will be shortened with this application.

Furthermore, the discomfort the patients are having will be relieved and a healthy relationship of the teeth to the jaw will be established. In addition to these, the completion of the treatment will be ensured to take place at a high level of patient cooperation.

Thanks to this invention, bone marrow- and adipose tissue-derived stem cells applied following the maxillary expansion—a frequently used method for the orthodontic treatment—made favorable contributions to the healing of the expanded bone tissue. The relapse occurring after the maxillary expansion treatment can be avoided by speeding up the bone healing time and increasing the quality of the bones. Thanks to this application, a shorter treatment period for patients undergoing the maxillary expansion treatment will be ensured and the patients will not have to use apparatus for a long period of time.

The invention claimed is:

1. A method for an orthodontic maxillary expansion treatment for a patient, consisting of:
   isolating a plurality of stem cells;
   expanding maxillary; and
   injecting the stem cells into a midpalatal suture region of the patient.

2. The method of claim 1, wherein the stem cells are bone marrow derived stem cells.

3. The method of claim 1, wherein the stem cells are adipose tissue derived stem cells.

4. The method of claim 1, wherein the method further includes injecting the stem cells into the midpalatal suture region at a dose of 1 million cells.

5. The method of claim 3, wherein the stem cells are adipose tissue derived mesenchymal stem cells (ATMSCs).

6. The method of claim 2, wherein the stem cells are bone marrow derived mesenchymal stein cells (BMMSCs).

7. The method of claim 3, wherein the method further includes injecting the stem cells into the midpalatal suture region at a dose of 1 million cells.

\* \* \* \* \*